(12) United States Patent
Stössel et al.

(10) Patent No.: US 7,745,627 B2
(45) Date of Patent: Jun. 29, 2010

(54) METHOD FOR THE PRODUCTION OF HETEROLEPTIC ORTHO-METALLATED ORGANOMETALLIC COMPOUNDS

(75) Inventors: Philipp Stössel, Frankfurt (DE); Arne Büsing, Frankfurt (DE); Ingrid Bach, Hofheim (DE)

(73) Assignee: Merck Patent GmbH, Darmstadt (DE)

( * ) Notice: Subject to any disclaimer, the term of this patent is extended or adjusted under 35 U.S.C. 154(b) by 1038 days.

(21) Appl. No.: 10/577,617

(22) PCT Filed: Oct. 21, 2004

(86) PCT No.: PCT/EP2004/011889

§ 371 (c)(1),
(2), (4) Date: Apr. 26, 2006

(87) PCT Pub. No.: WO2005/042548

PCT Pub. Date: May 12, 2005

(65) Prior Publication Data

US 2007/0135635 A1    Jun. 14, 2007

(30) Foreign Application Priority Data

Oct. 30, 2003    (DE) ................. 103 50 606

(51) Int. Cl.
C07F 15/00 (2006.01)
C07F 9/547 (2006.01)
(52) U.S. Cl. .................. 546/2; 546/4; 556/13
(58) Field of Classification Search .......... 546/2, 546/4; 556/13
See application file for complete search history.

(56) References Cited

U.S. PATENT DOCUMENTS

| | | | |
|---|---|---|---|
| 4,539,507 A | 9/1985 | VanSlyke et al. | |
| 5,151,629 A | 9/1992 | VanSlyke | |
| 6,870,054 B1 * | 3/2005 | Deaton et al. ................. | 546/10 |
| 2003/0162299 A1 | 8/2003 | Hsieh et al. | |
| 2004/0077862 A1 | 4/2004 | Stossel et al. | |
| 2004/0138455 A1 | 7/2004 | Stossel et al. | |
| 2005/0131232 A1 | 6/2005 | Stössel et al. | |
| 2006/0071206 A1 | 4/2006 | Stossel et al. | |

FOREIGN PATENT DOCUMENTS

| | | |
|---|---|---|
| DE | 102 23 337 | 12/2003 |
| DE | 102 51 986 | 5/2004 |
| DE | 103 14 102 | 10/2004 |
| EP | 1 239 526 | 9/2002 |
| WO | WO-01/41512 | 6/2001 |
| WO | WO-02/060910 | 8/2002 |
| WO | WO-02/068435 | 9/2002 |

\* cited by examiner

*Primary Examiner*—Charanjit S Aulakh
(74) *Attorney, Agent, or Firm*—Connolly Bove Lodge & Hutz LLP

(57) ABSTRACT

The invention relates to a method for the production of high-purity, heteroleptic, orth-etallated, organometallic compounds of application as a functional material for colouring components in a wide range of applications within the widest sense of the electronics industry. A method is thus used for the cleavage of a bridged metal dimer with organometallic substances. Dihalo complexes, which may be used as monomers for polymerisations, in particular, may be produced thus.

11 Claims, No Drawings

METHOD FOR THE PRODUCTION OF HETEROLEPTIC ORTHO-METALLATED ORGANOMETALLIC COMPOUNDS

RELATED APPLICATION

This application is a national stage application (under 35 U.S.C. 371) of PCT/EP2004/011889 filed Oct. 21, 2004 which claims benefit to German application 103 50 606.3 filed Oct. 30, 2003.

Organometallic compounds—specifically compounds of the $d^8$ metals—are required as functional materials for use as colouring components in a number of different applications which can be ascribed in the broadest sense to the electronics industry. In the case of the organic electroluminescent devices based on purely organic components (general description of the structure see: U.S. Pat. Nos. 4,539,507 and 5,151,629) and individual components thereof, the organic light-emitting diodes (OLEDs), the market introduction has already taken place, as confirmed, for example, by the automobile radios with an OLED display from Pioneer or the digital camera with an OLED display from Kodak. Further products of this type are just about to be introduced. Nevertheless, significant improvements are still necessary here in order to make these displays a true competitor to the liquid-crystal displays (LCDs) which currently dominate the market, or to surpass them.

A development in this respect which has emerged in recent years is the use of organometallic complexes which exhibit phosphorescence instead of fluorescence (M. A. Baldo et al., *Appl. Phys. Lett.* 1999, 75, 4-6). For theoretical spin-statistical reasons, an up to four-fold energy and power efficiency is possible using such compounds. Whether this development will succeed, however, is on the one hand highly dependent on whether it is possible to find corresponding device compositions which are also able to implement these advantages (triplet emission=phosphorescence compared with singlet emission=fluorescence) in OLEDs. Essential conditions for practical application which may be mentioned here are, in particular, a long operating lifetime, high thermal stability and a low use and operating voltage. On the other hand, efficient chemical access to the corresponding high-purity metal complexes, in particular to organoiridium compounds, must be possible. This is of crucial importance for successful utilisation of the said class of compounds, in particular taking into account the scarcity of iridium.

The literature has described a number of processes for the preparation of bis- and tris-ortho-metallated organometallic compounds, which will be explained in greater detail below with reference to the example of corresponding iridium complexes.

The closest prior art for the synthesis of homoleptic, tris-ortho-metallated iridium complexes, such as, for example, fac-tris[2-(2-pyridinyl-κN)phenyl-κC]iridium(III), is described in WO 02/060910 and the unpublished application DE 10314102.2. These processes give very good yields of high-purity complexes, in the further purification of which chromatographic methods are unnecessary. However, these methods are not suitable for the synthesis of heteroleptic tris-ortho-metallated iridium complexes since the three ligands are introduced in the same reaction step and different ligands result in mixtures here.

However, heteroleptic ortho-metallated iridium complexes are also of major interest for the application: firstly, the different ligands enable different electronic properties to be incorporated into a single complex. Thus, different ligands enable, for example, fine tuning of the emission colour and/or of the charge-transport properties. A further property that these heteroleptic complexes generally exhibit is an elevated glass transition temperature. This is a crucial advantage, in particular for low-molecular-weight compounds, since this is a prerequisite for use of these compounds in OLEDs. Furthermore, heteroleptic complexes generally have better solubility and can consequently be purified more easily, for example by recrystallisation, or also processed from solution. In particular, heteroleptic complexes which have been functionalised with two polymerisable groups can, as monomers, be incorporated covalently into polymers. Polymers offer the advantage over vapour-depositable, low-molecular-weight compounds that they can be processed from solution, which should offer significant advantages in the long term over technologically complex vacuum vapour deposition processes. The use of iridium complexes of this type in polymers is being discussed as the next step in the further development of light-emitting polymers.

It would therefore be desirable to have available a method which has broad applicability and allows access to heteroleptic iridium complexes, in particular also to copolymerisable heteroleptic iridium complexes.

Further processes for the synthesis of homoleptic, ortho-metallated iridium complexes which can also be adapted for the synthesis of heteroleptic complexes are described in the literature:

Homoleptic complexes can be obtained, for example, by reaction of di-(μ-chloro)-tetrakis[2-(2-pyridinyl-κN)phenyl-κC]diiridium(III) with phenylpyridine and twice the molar amount of silver trifluoromethanesulfonate, based on di-(μ-chloro)tetrakis[2-(2-pyridinyl-κN)phenyl-κC]diiridium(III). After chromatographic purification, the authors obtain tris[2-(2-pyridinyl-κN)phenyl-κC]iridium(III) in a yield of 75% (M. G. Colombo et al., *Inorg. Chem.* 1994, 33, 545-550). Heteroleptic complexes are also accessible analogously thereto if a different ligand is employed instead of phenylpyridine (for example A. Beeby et al., *J. Mater. Chem.* 2003, 13, 80-83). Besides the chromatographic purification, which is carried out with the aid of environmentally harmful halogenated hydrocarbons, the use of the large amount of silver salts is disadvantageous. Firstly, the use of expensive silver compounds makes the synthesis additionally expensive. Furthermore, residual traces of silver chloride produce colloidal silver, which can only be separated off with difficulty or not at all, meaning that the material prepared in this way is not very suitable for use in OLEDs since it is generally recognised that high-purity material is required for this purpose. In addition, this synthetic route is generally problematic since, according to Thompson et al. (WO 01/41512), it only works well for a few selected ligands.

A further possible synthesis likewise starts from di-(μ-chloro)tetrakis[2-(2-pyridinyl-κN)phenyl-κC]diiridium(III): this is reacted directly with a further ligand, as described, for example, in EP 1239526 and WO 01/41512. In both cases, the additional ligand is a β-diketonate or a related compound. These complexes are heteroleptic, ortho-metallated compounds, but not tris-ortho-metallated complexes. However, tris-ortho-metallated complexes are preferred in the long term since they are thought, without wishing to be tied to a particular theory, to have higher stabilities and thus longer lifetimes than compounds which contain β-diketonates or similar ligands.

Reaction of the β-diketonate-containing complexes described above with a further ligand also gives access to tris-ortho-metallated iridium complexes, as described, for example, in U.S. 20030162299. However, this method exhibits significant disadvantages: firstly, a relatively large number of steps are necessary starting from iridium-containing starting materials (synthesis of the bridged iridium dimer $[L_2Ir(\mu\text{-}Cl)]_2$, reaction with the β-diketonate, subsequently further reaction with another ligand). Furthermore, the yields, at about 45%, are very low, and chromatographic methods are necessary for the purification, which makes this process of little interest for industrial applications. In particular in view of the rarity of iridium, it is desirable to have available a resource-protecting method in which iridium-containing starting materials are only employed in a few steps and in which these steps each proceed with high yields.

Dihalogenated, heteroleptic, tris-ortho-metallated iridium complexes are furthermore accessible by halogenation of a corresponding homoleptic complex, as described in WO 02/068435. However, this process gives ready access, in particular, to complexes whose ligands are based on the same ligand system. Although heteroleptic complexes having different ligand systems can also be dihalogenated, there is a lack of specific and good access to the corresponding heteroleptic starting compounds.

A further method for obtaining heteroleptic iridium complexes is described in the unpublished application DE 10223337.3, in which homo- and heteroleptic complexes are obtained from the bridged iridium dimer $[L_2Ir(\mu\text{-}Cl)]_2$ by carrying out the reaction of the dimer with the ligand in the presence of a Lewis acid. This method can be used with good results for a multiplicity of ligands. However, it was striking that the synthesis worked less well for other ligands or under certain circumstances did not work at all or gave product mixtures. Thus, for example, in the case of the reaction with pyridylbenzothiophene, the product was obtained in a purity of only 91% and had to be purified by chromatography.

The synthesis of bis-ortho-metallated, heteroleptic palladium complexes is also described in the literature (P. Jolliet et al., *Inorg. Chem.* 1996, 35, 4883). The starting material here is a chloro-bridged binuclear palladium complex. This is reacted with $Et_2S$ to give the corresponding monocyclic complex $[PdL(Et_2S)Cl]$, which is then reacted further with the lithium derivative of the second ligand. However, very poor yields (17-26%) were achieved in this reaction. In addition, the complex had to be purified by chromatography, which is unsuitable for industrial application, and this purification was carried out using solvents which are dubious from a health point of view, such as chlorinated hydrocarbons.

The object of this invention was thus firstly to provide a broadly usable process for the synthesis of heteroleptic metal complexes. In particular, the aim was to investigate the provision of a wide variety of homo- and heteroleptic, functionalised, copolymerisable complexes. A further object of the invention was to find a process which does not require complex purification by means of chromatographic methods. Surprisingly, it has now been found that heteroleptic complexes of this type are obtained in high purity and in good yield if the readily accessible, bridged metal dimer $[L_nM(\mu\text{-}Y)]_2$ is reacted with a reactive organometallic compound of a further ligand. It has been found here that this process generally works very well, irrespective of the ligand employed. This process gives broadly usable access to heteroleptic iridium complexes which have purities of >99.0%. Given a suitable choice of the reaction parameters, such as temperature, reaction times and solvent, products are obtained reproducibly in a yield of 90-95% which can be purified by recrystallisation without the use of chromatographic methods. In particular, this method also gives simple and efficient access to dihalogenated iridium complexes which can be used as monomers for the polymerisation.

The present invention relates to a process for the preparation of compounds (I)

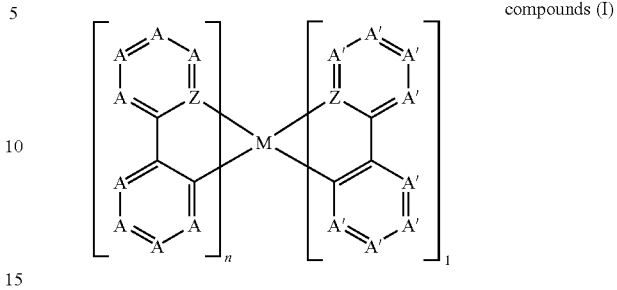

compounds (I)

where the following applies to the symbols and indices used:
M is, identically or differently on each occurrence, Rh, Ir, Pd or Pt;
Z is, identically or differently on each occurrence, N or P, preferably N;
A, A' is, identically or differently on each occurrence, N, C—H or C—R or C—R'; or alternatively two adjacent ring atoms A-A or A'-A' on each occurrence, identically or differently, stand for S, O, Se or N—$R^1$, with the proviso that these units do not occur more than once per ring; A or A' is preferably C—H or C—R or C—R'; preference is furthermore given to two adjacent ring atoms A-A or A'-A' equal to S;
R, R' is, identically or differently on each occurrence, F, Cl, Br, $NO_2$, CN, a straight-chain, branched or cyclic alkyl or alkoxy group having 1 to 20 C atoms, where one or more non-adjacent $CH_2$ groups may be replaced by —$CR^1$=$CR^1$—, —C≡C—, —O—, —S—, —$NR^1$—, or —$CONR^1$— and where one or more H atoms may be replaced by F, or an aryl, heteroaryl, aryloxy or arylamino group having 4 to 14 C atoms, which may be substituted by one or more non-aromatic radicals R, where a plurality of substituents R, both on the same ring and also on the two different rings, together may in turn define a further mono- or polycyclic, aliphatic or aromatic ring system;
$R^1$ are, identically or differently on each occurrence, H or an aliphatic or aromatic hydrocarbon radical having 1 to 20 C atoms;
n is 1 for M=Pd or Pt and is 2 for M=Rh or Ir;

by reaction of a compound (Ia)

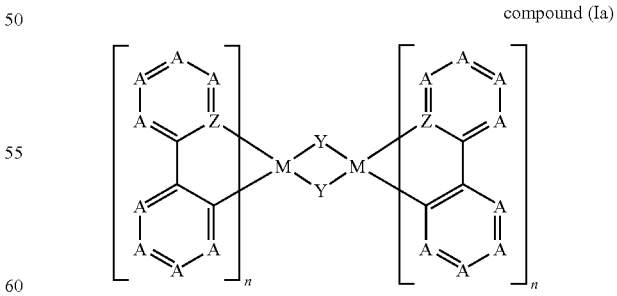

compound (Ia)

in which:
Y is on each occurrence, identically or differently, F, Cl, Br, I, $OR^1$, $R^1COO$, $SR^1$, $N(R^1)_2$;
and the other symbols and indices are as defined for compound (I), characterised in that compound (Ia) is reacted with an organometallic compound (Ib)

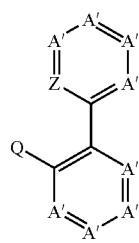

compound (Ib)

where Q stands for an alkali metal, an alkaline-earth metal or alkaline-earth metal halide, trialkyltin or zinc or a zinc halide and may optionally also carry further organic radicals, and the other symbols and indices have the meaning given under compound (I).

It should be particularly emphasised here that although homoleptic complexes are also accessible by this process, the special feature of the process is, however, that it allows clean access to heteroleptic complexes. A heteroleptic complex (compound I) is obtained if the ligands in compound (Ia) are not identical to the ligand formed from compound (Ib) by coordination to the central atom.

Binuclear metal complexes which are bridged by groups Y, such as compound (Ia), are abbreviated below to "bridged metal dimer", or $[L_nM(\mu-Y)]_2$, where L generally stands for a ligand from the class of the phenylpyridines or derivatives, as defined above under formula (I).

The process according to the invention is explained by scheme 1.

Scheme 1:

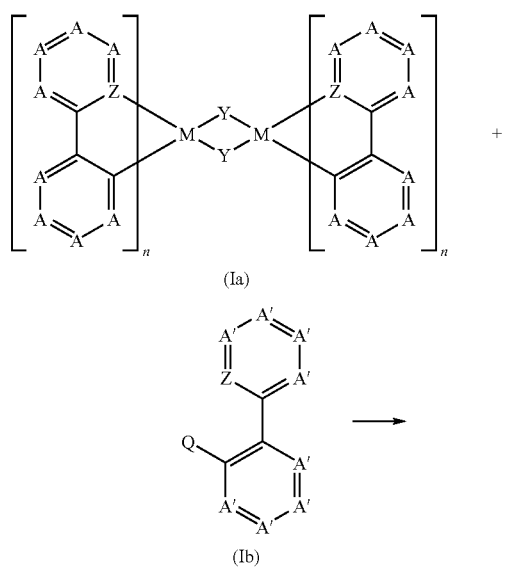

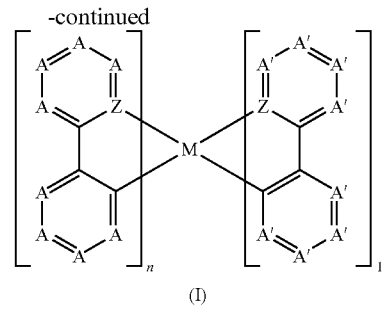

(I)

Metal-containing starting materials according to the invention are binuclear metal complexes which conform to the formula (Ia). These are generally readily accessible. Preferred metal-containing starting materials are binuclear metal complexes which are bridged via groups Y, where Y on each occurrence, identically or differently, stands for F, Cl, Br or $OR^1$. Particularly preferred metal-containing starting materials are binuclear metal complexes which are bridged via groups Y, where Y stands for Cl. The synthesis of such compounds is described, for example, in J. Sprouse et al., *J. Am. Chem. Soc.* 1984, 106, 6647. This description is part of the present invention by quotation.

Organometallic compounds (Ib) according to the invention are compounds which are derived from the desired ligand through the fact that an alkali metal, an alkaline-earth metal, tin or zinc is bonded to the carbon atom which is bonded to the central atom in the complex, where these metals may optionally also carry further organic radicals, such as, for example, aryl or alkyl substituents, or inorganic radicals, such as, for example, halides. Covalent multicentre bonds are also expressly allowed here. Preferred organometallic compounds are those which contain an alkali metal or an alkaline-earth metal in this position. Particular preference is given here to lithium, sodium or magnesium; very particular preference is given to magnesium. Of the organomagnesium compounds, preference is given to so-called Grignard compounds, which, besides the magnesium-aryl bond, also carry a halide, i.e. compounds of the aryl-Mg halide type.

The molar ratio according to the invention of bridged metal dimer, $[L_nM(\mu-Cl)]_2$, compound (Ia), to the organometallically functionalised ligand, compound (Ib), is 1:2 to 1:50; preference is given to a ratio of 1:2 to 1:25; particular preference is given to a ratio of 1:2 to 1:10.

Preferred reaction media are open-chain or cyclic ethers, such as, for example, diethyl ether, methyl tert-butyl ether, THF, dioxane, tetrahydropyran or the like, oligo- or polyethers, for example poly(ethylene glycol) dimethyl ether, or also HMPTA or open-chain or cyclic dialkylureas, such as, for example, DMPU or N,N'-dimethyl-ethyleneurea (1,3-dimethylimidazolidin-2-one).

In accordance with the invention, the reaction is carried out in a temperature range from −78° C. to 150° C., preferably in the range from −10° C. to 70° C.

In accordance with the invention, the reaction is carried out over the course of 0.5 to 48 h, preferably over the course of 3 to 24 h. A reaction time less than that stated can result in incomplete conversion of the metal-containing starting material employed, which results in losses of yield and in contamination of the product.

The process described in this invention furthermore offers, in particular, the advantage that a wide variety of heteroleptic dihalogenated complexes, as can be used, for example, as monomers for polymerisations, are accessible simply and in high purity.

A further aspect of this invention is therefore a process according to scheme 2 or scheme 3 for the synthesis of dihalogenated tris-ortho-metallated rhodium and iridium complexes or monohalogenated bis-ortho-metallated palladium and platinum complexes, starting from the bridged metal dimer [L$_n$M(μ-Y)]$_2$, which carries a hydrogen on the phenyl ring in the para-position to the coordinating C atom; this position is halogenated in the first step and, in accordance with the first aspect of the invention, reacted with an organometallic derivative of a further ligand in a further step. The basic structure of the further ligand here may be identical to or different from the structure of the first ligand.

Scheme 2:

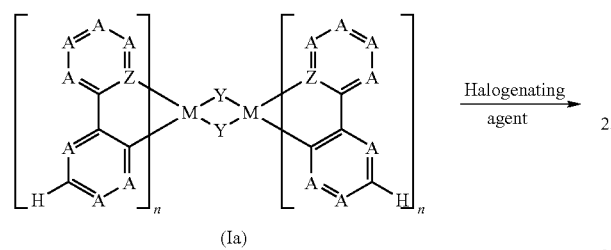
(Ia)

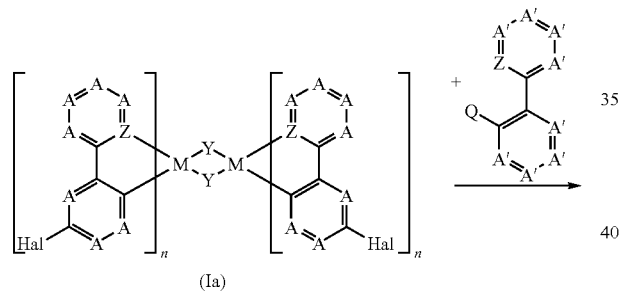
(Ia)

Scheme 3:

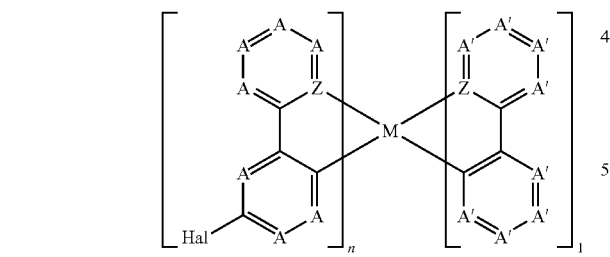
(Ia)

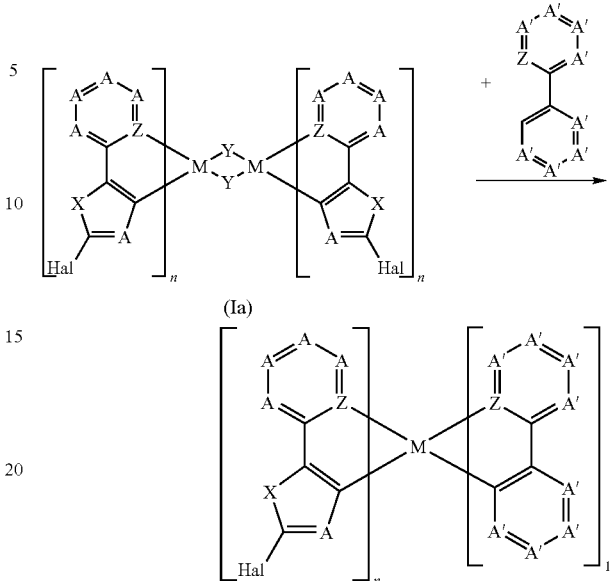
(Ia)

where the following applies to the symbols and indices used:
M, Z, A, A', R, R', R$^1$, Q, Y and n have the same meaning as indicated under formula (I), (Ia) and (Ib);
Hal is on each occurrence, identically or differently, Cl, Br, I;
X is on each occurrence, identically or differently, N—R$^1$, O, S or Se, preferably S.

The way in which the halogenation of the bridged metal dimers [L$_n$M(μ-Y)]$_2$ (first step in scheme 2 or scheme 3) can be carried out is described, for example, in WO 02/060910 and in the unpublished application DE 10251986.2.

The organometallic derivatives (Ib) of the ligand employed for the process according to scheme 1, scheme 2 and scheme 3 can easily be produced by methods as are generally familiar to the person skilled in the art. These compounds can be prepared, for example, from the corresponding halogenated compounds, preferably from the chlorinated, brominated or iodinated compounds, by metal-halogen exchange. Reactions with elemental magnesium, sodium, lithium or zinc, but also, for example, the reaction with alkyllithium compounds, as are generally known to the person skilled in the art, are, for example, available for this purpose. The corresponding halogenated derivatives of the ligand can be obtained by direct halogenation of the ligand, for example if it is an electron-rich heterocycle. Thus, for example, thiophene- or benzothiophene-containing ligands can be brominated directly. Another possibility consists in already introducing the halogen functionality into the precursors of the ligand synthesis. For example, 2-(ortho-chlorophenyl)pyridine can be synthesised in this way from 2-bromopyridine and 2-chlorobenzeneboronic acid by Suzuki coupling. The chlorine group can then be exchanged, for example, for magnesium or lithium.

The compounds of the formula (I) described in the prior art were hitherto only accessible in yields of about 50% or less and had to be purified by complex chromatographic methods, frequently using environmentally harmful, halogenated solvents. However, the process according to the invention enables compounds (I) to be obtained in purities of greater than 99.0% without chromatographic methods being necessary.

The process according to the invention offers the advantage of making a wide range of heteroleptic iridium complexes accessible in high purity. It should be particularly emphasised here that transition-metal salts, such as, for example, silver salts, which remain in the metal complex as an impurity afterwards, do not have to be employed for the synthesis. Compared with the process in DE 10223337.3, the process according to the invention offers the advantage of giving very good results for a wider range of ligands. In particular, this process offers access to copolymerisable iridium complexes which were hitherto not accessible to this extent and in this variety. Since iridium complexes which are covalently bonded to polymers are re-garded as starting materials for the further development of light-emitting polymers, the process, which provides the basic building blocks (monomers) for this purpose, represents an important step in this direction.

The present invention is explained in greater detail by the following examples, but without wishing to be restricted thereto. This enables the person skilled in the area of organic and organometallic synthesis to carry out the reactions according to the invention on further systems—as described above—without further inventive step.

EXAMPLES

The following syntheses were carried out, apart from the work-up, under a dry nitrogen or argon atmosphere using anhydrous solvents. The starting materials used (iridium(III) chloride.n $H_2O$ and 2-phenylpyridine, abbreviated to PPy below) were purchased commercially from ABCR and used without further purification. The following syntheses were carried out in accordance with the literature: [Di(μ-chloro) tetrakis[(2-pyridinyl-κN-phenyl)-κC]diiridium(III) (abbreviated to [(PPy)$_2$Ir(μ-Cl)]$_2$ below) and derivatives of this compound in accordance with J. Sprouse et al., *J. Am. Chem. Soc.* 1984, 106, 6647; 2-(2'-pyridyl)benzothiophene (abbreviated to BTP below) in accordance with EP 1191612; and 2-(2'-chloro-phenyl)pyridine in accordance with V. Martinez-Barrasa et al., *Org. Lett.* 2000, 2, 3933.

Example 1

Bromination of [(PPy)$_2$Ir(μ-Cl)]$_2$

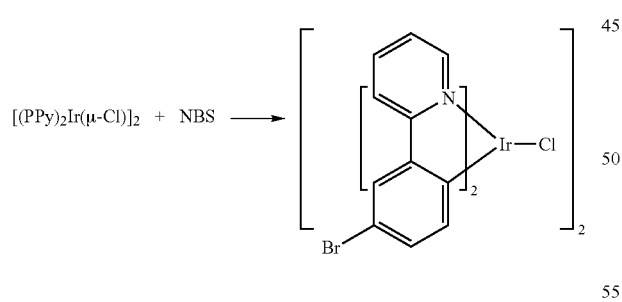

11.6 g (10.8 mmol) of [(PPy)$_2$Ir(μ-Cl)]$_2$ were dissolved in 370 ml of dichloromethane in a 1000 ml four-necked flask with mechanical stirrer, argon blanket and internal thermometer and saturated with argon. 7.7 g (43.1 mmol) of N-bromosuccinimide and 771 mg of FeCl$_3$ were added, and the solution was stirred overnight with exclusion of light. 75 ml of EtOH and 45 ml of water were then added, and the dichloromethane was removed under reduced pressure. The precipitate was filtered off with suction, washed with EtOH and heptane and dried under reduced pressure, giving 14.9 g (10.7 mmol, 99.4% of theory) of the product [(Br-PPy)$_2$Ir(μ-Cl)]$_2$ in a purity of 99% according to NMR. The corresponding brominated ligand is abbreviated to Br-PPy below. $^1$H-NMR (500 MHz, DMSO-d$_6$): [ppm] 5.54 (d, J=8.4 Hz, 2H), 6.15 (d, J=8.4 Hz, 2H), 6.88 (d, J=8.0 Hz, 2H), 6.95 (d, J=8.1 Hz, 2H), 7.52 (t, J=5.7 Hz, 2H), 7.62 (t, J=6.4 Hz, 2H), 7.97 (s, 2H), 8.03 (s, 2H), 8.05 (t, J=7.7 Hz, 2H), 8.13 (t, J=7.4 Hz, 2H), 8.30 (d, J=8.4 Hz, 2H), 8.38 (d, J=8.1 Hz, 2H), 9.51 (d, J=5.0 Hz, 2H), 9.76 (d, J=5.4 Hz, 2H).

Example 2

Synthesis of 3-bromo-2-(2'-pyridyl)benzothiophene

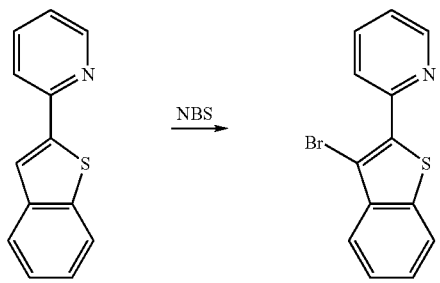

2-(2'-Pyridyl)benzothiophene BTP (4 g, 19 mmol) were dissolved in 75 ml of DMF in a 250 ml four-necked flask with mechanical stirrer. 3.55 g (20 mmol) of N-bromo-succinimide were added with exclusion of light, and the reaction mixture was stirred at room temperature for 12 h. 100 ml of $H_2O$ were added, the precipitate was filtered off with suction, washed with methanol and dried under reduced pressure. Further purification Was carried out by recrystallisation from ethanol, giving 3.56 g (65% of theory) of the product. $^1$H-NMR (500 MHz, CDCl$_3$): [ppm] 7.29 (ddd, J=1.0 Hz, 4.9 Hz, 7.4 Hz, 1H), 7.41-7.48 (m, 2H), 7.81 (td, J=1.6 Hz, 7.4 Hz, 1H), 7.85 (d, J=8 Hz, 1H), 8.50 (d, J=8 Hz, 1H), 8.69-8.70 (m, 1H).

Example 3

Synthesis of Ir[(Br-PhPy)$_2$(BTP)]

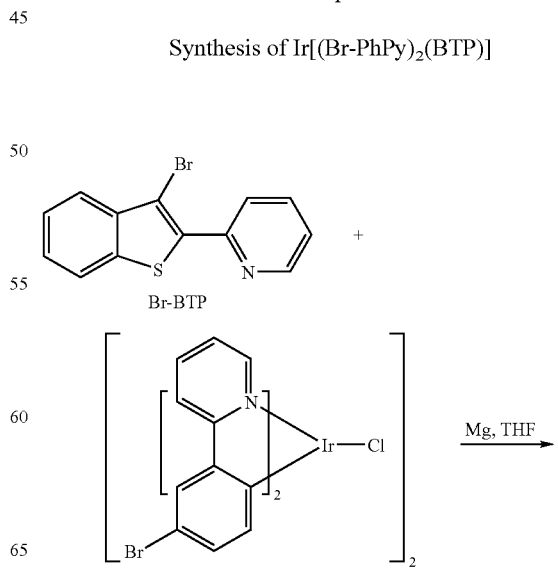

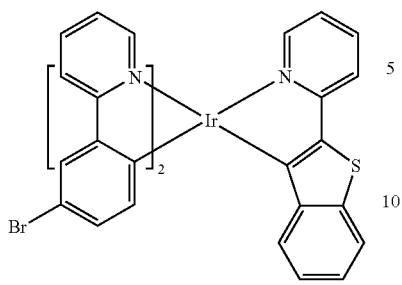

3-Bromo-2-(2'-pyridylbenzothiophene (Br-BTP) (2.8 g, 9.7 mmol) and 1,2-dichoro-ethane (150 μl, 1.9 mmol) dissolved in 50 ml of absolute THF were added dropwise to a suspension of 233 mg (9.7 mmol) of magnesium in 3 ml of THF in a dry 100 ml three-necked flask, and the mixture was boiled under reflux for 3 h. 3 g (2.4 mmol) of [(Br-PPy)$_2$Ir(μ-Cl)]$_2$ were suspended in 190 ml of absolute THF in a dry 250 ml four-necked flask with internal thermometer and argon blanket and cooled to 0° C. The Grignard solution was added dropwise to this suspension of the iridium complex. After 30 min., the cooling bath was removed, and the mixture was stirred overnight at RT. The mixture was cooled to −10° C., and 20 ml of iso-PrOH and H$_2$O were added until precipitation was complete. The precipitate was filtered off with suction and dried. The yield was 3.91 g (4.6 mmol, 96.2% of theory) with a purity of 98.9% according to HPLC. $^1$H-NMR (500 MHz, DMSO-d$_6$): [ppm] 6.29 (d, J=8.0 Hz, 1H), 6.37 (d, J=8.0 Hz, 1H), 6.75-6.78 (m, 4H), 6.91-6.94 (m, 2H), 7.02 (dd, J=2.0 Hz, 7.7 Hz, 1H), 7.15 (t, J=7.0 Hz, 1H), 7.50 (td, J=1.6 Hz, 8.0 Hz, 1H), 7.57-7.69 (m, 4H), 7.70-7.82 (m, 6H), 8.04 (d, J=5.0 Hz, 1H).

Example 4

Synthesis of Ir(Br-PPy)$_2$(PPy)

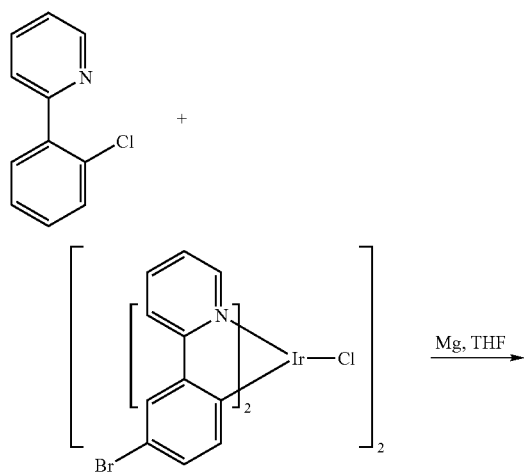

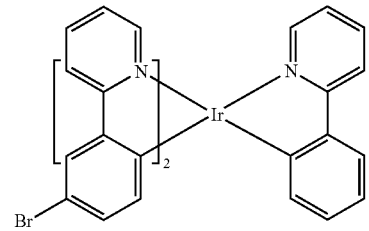

2-(2'-Chlorophenyl)pyridine (682 mg, 3.6 mmol) and 1,2-dichoroethane (30 μl, 0.4 mmol) were dissolved in 20 ml of absolute THF in a dry 100 ml three-necked flask, a suspension of 90 mg (4 mmol) of magnesium in 5 ml of THF was added, and the mixture was boiled under reflux for 3 h. 600 mg (0.5 mmol) of [(Br-PPy)$_2$Ir(μ-Cl)]$_2$ were dissolved in 40 ml of absolute THF in a dry 250 ml four-necked flask with internal thermometer and argon blanket and cooled to 0° C. The Grignard solution was added dropwise to this solution of the iridium complex. After 30 min., the cooling bath was removed, and the mixture was stirred overnight at RT. The mixture was cooled to −10° C., and 5 ml of $^i$PrOH and H$_2$O were added. The precipitated product was dissolved in THF and dichloromethane, washed with water, dried over Na$_2$SO$_4$, and the solvents were removed under reduced pressure. Purification was carried out by extraction from boiling heptane. The yield was 791 mg (0.97 mmol, 97.3% of theory) with a purity of 99.4% according to HPLC. $^1$H-NMR (500 MHz, CDCl$_3$): [ppm] 6.27 (d, J=8.4 Hz, 1H), 6.44 (d, J=7.7 Hz, 1H), 6.76 (q, J=7.4 Hz, 2H), 6.90-6.92 (m, 3H), 6.95-7.04 (m, 3H), 7.49 (t, J=7.7 Hz, 1H), 7.54-7.58 (m, 2H), 7.64 (td, J=1.4 Hz, 7.4 Hz, 1H), 7.72-7.78 (m, 5H), 7.90 (d, J=5.4 Hz, 1H), 7.94 (d, J=8.1 Hz, 1H), 8.07 (d, J=6.1 Hz, 1H).

Example 5

Comparative Example

The synthesis of the target structure from Example 3 was repeated using the process described in DE 10223337.3 as closest prior art. For this purpose, [(Br-PPy)$_2$Ir(μ-Cl)]$_2$ (2.93 g, 2.5 mmol) was reacted with 25 equivalents of BTP (2.11 g, 10 mmol) with addition of 0.73 g (5.5 mmol) of aluminum (III) chloride in 75 ml of decalin. The reaction mixture was stirred at 180° C. for 48 h. The reaction mixture was subsequently poured into a mixture of 300 ml of ethanol and 300 ml of 1M hydrochloric acid. The mixture was stirred for 5 min., then the microcrystalline precipitate was filtered off with suction through a glass suction filter (P4), washed with ethanol/water (1:1) and ethanol and dried under reduced pressure. The yield was 3.14 g (74% of theory) with a purity of 91%. The product had to be separated off from decomposition products, which were not characterised in greater detail, by chromatography (silica, hexane:ethyl acetate 6:1).

The invention claimed is:

1. A process for the preparation of compounds (I)

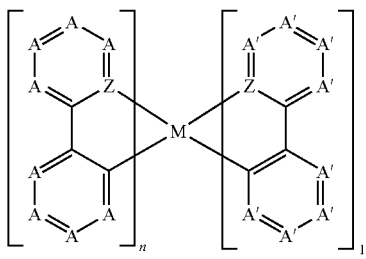

compound (I)

wherein

M is, identically or differently on each occurrence, Rh, Ir, Pd or Pt;

Z is, identically or differently on each occurrence, N or P;

A, A' is, identically or differently on each occurrence, N, C—H or C—R or C—R'; or alternatively two adjacent ring atoms A-A or A'-A' on each occurrence, identically or differently, stand for S, O, Se or N—R$^1$, with the proviso that these units do not occur more than once per ring;

R, R' is, identically or differently on each occurrence, F, Cl, Br, NO$_2$, CN, a straight-chain, branched or cyclic alkyl or alkoxy group having 1 to 20 C atoms, where one or more non-adjacent CH$_2$ groups may be replaced by —CR$^1$=CR$^1$—, —C≡C—, —O—, —S—, —NR$^1$—, or —CONR$^1$— and where one or more H atoms may be replaced by F, or an aryl, heteroaryl, aryloxy or arylamino group having 4 to 14 C atoms, which may be substituted by one or more non-aromatic radicals R; where a plurality of substituents R on the same ring together may in turn define a further mono- or polycyclic, aliphatic or aromatic ring system;

R$^1$ is, identically or differently on each occurrence, H or an aliphatic or aromatic hydrocarbon radical having 1 to 20 C atoms;

n is 1 for M=Pd or Pt and is 2 for M=Rh or Ir;

which comprises reacting a compound (Ia)

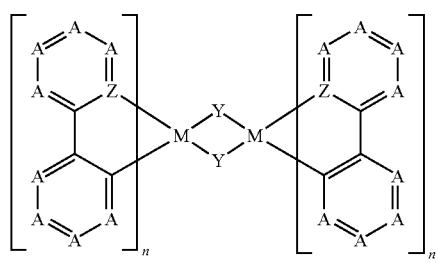

compound (Ia)

wherein

Y is on each occurrence, identically or differently, F, Cl, Br, I, OR$^1$, R$^1$COO, SR$^1$, N(R$^1$)$_2$;

and the other symbols and indices are as defined for compound (I), with an organometallic compound (Ib)

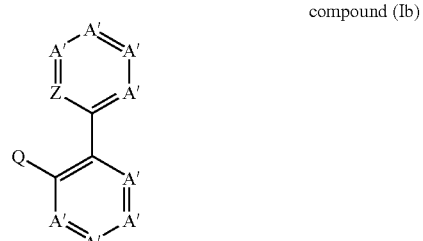

compound (Ib)

where Q stands for an alkali metal, an alkaline-earth metal or alkaline-earth metal halide, trialkyltin or zinc or a zinc halide, which may optionally also be substituted by further organic groups, and the other symbols and indices have the meaning given for compound (I).

2. The process according to claim 1, wherein metal-containing starting materials are binuclear metal complexes of the formula (Ia), in which Y on each occurrence, identically or differently, denotes F, Cl, Br or OR$^1$.

3. The process according to claim 1, wherein Q represents an alkali metal or an alkaline-earth metal or alkaline-earth metal halide.

4. The process according to claim 3, wherein Q stands for lithium, sodium or magnesium or a magnesium halide.

5. The process according to claim 4, wherein Q stands for magnesium or a magnesium halide.

6. The process according to claim 1, wherein the molar ratio of compound (Ia) to compound (Ib), is 1:2 to 1:50.

7. The process according to claim 1, wherein said reaction of compound (Ia) with compound (Ib) is performed in a solvent selected from the group consisting of open-chain or cyclic ethers, open-chain or cyclic dialkylureas or HMPTA.

8. The process according to claim 1, wherein the reaction is carried out in a temperature range from −78° C. to 150° C.

9. The process according to claim 1, wherein the reaction is carried out over the course of 0.5 to 48 h.

10. Process for the synthesis of dihalogenated tris-ortho-metallated rhodium and iridium complexes or monohalogenated bis-ortho-metallated palladium and platinum complexes, wherein a process according to claim 1 is used in one reaction step.

11. The process according to claim 10, wherein it is carried out in accordance with scheme 2

Scheme 2:

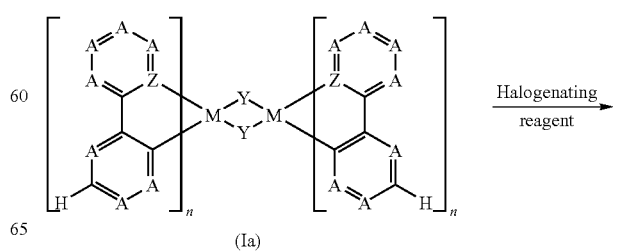

-continued

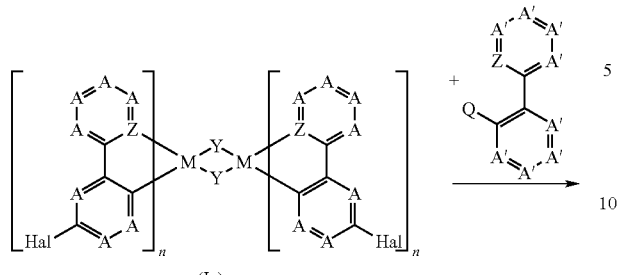

(Ia)

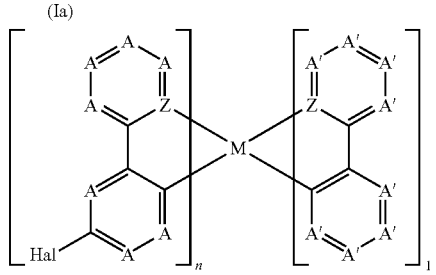

or scheme 3

Scheme 3:

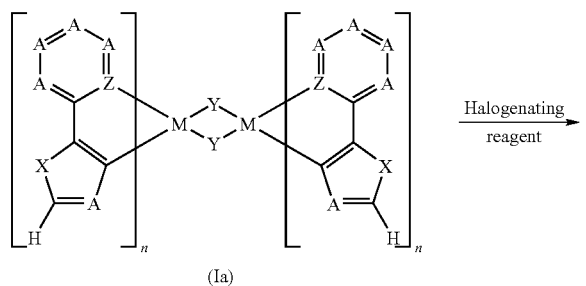

(Ia)

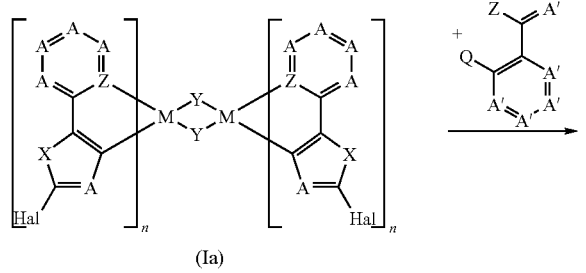

(Ia)

-continued

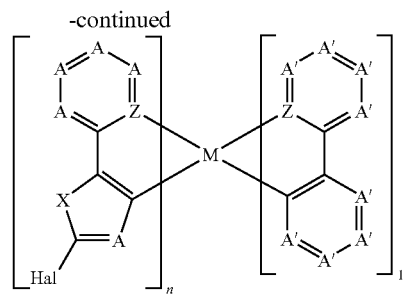

wherein
M is, identically or differently on each occurrence, Rh, Ir, Pd or Pt;
Z is, identically or differently on each occurrence, N or P;
A, A' is, identically or differently on each occurrence, N, C—H or C—R or C—R'; or alternatively two adjacent ring atoms A-A or A'-A' on each occurrence, identically or differently, stand for S, O, Se or N—$R^1$, with the proviso that these units do not occur more than once per ring;
R, R' is, identically or differently on each occurrence, F, Cl, Br, $NO_2$, CN, a straight-chain, branched or cyclic alkyl or alkoxy group having 1 to 20 C atoms, where one or more non-adjacent $CH_2$ groups may be replaced by —$CR^1$=$CR^1$—, —C≡C—, —O—, —S—, —$NR^1$—, or —$CONR^1$— and where one or more H atoms may be replaced by F, or an aryl, heteroaryl, aryloxy or arylamino group having 4 to 14 C atoms, which may be substituted by one or more non-aromatic radicals R; where a plurality of substituents R on the same ring together may in turn define a further mono- or polycyclic, aliphatic or aromatic ring system;
$R^1$ is, identically or differently on each occurrence, H or an aliphatic or aromatic hydrocarbon radical having 1 to 20 C atoms;
Y is on each occurrence, identically or differently, F, Cl, Br, I, $OR^1$, $R^1COO$, $SR^1$, $N(R^1)_2$;
n is 1 for M=Pd or Pt and is 2 for M=Rh or Ir;
Q stands for an alkali metal, an alkaline-earth metal or alkaline-earth metal halide, trialkyltin or zinc or a zinc halide, which may optionally also be substituted by further organic groups
Hal is on each occurrence, identically or differently, Cl, Br, I; and
X is on each occurrence, identically or differently, N—$R^1$, O, S or Se.

\* \* \* \* \*